(12) United States Patent
Perszyk et al.

(10) Patent No.: US 10,925,640 B2
(45) Date of Patent: Feb. 23, 2021

(54) FLEXIBLE TORQUE CABLE FOR DELIVERY OF MEDICAL DEVICES

(71) Applicant: St. Jude Medical, Cardiology Division, Inc., St. Paul, MN (US)

(72) Inventors: Brian Perszyk, Shoreview, MN (US); Caytlin Gale, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 163 days.

(21) Appl. No.: 15/903,432

(22) Filed: Feb. 23, 2018

(65) Prior Publication Data

US 2018/0235658 A1 Aug. 23, 2018

Related U.S. Application Data

(60) Provisional application No. 62/462,661, filed on Feb. 23, 2017, provisional application No. 62/478,883, filed on Mar. 30, 2017, provisional application No. 62/503,061, filed on May 8, 2017.

(51) Int. Cl.

| | |
|---|---|
| *A61B 1/32* | (2006.01) |
| *A61B 17/34* | (2006.01) |
| *A61M 25/09* | (2006.01) |
| *A61B 17/00* | (2006.01) |
| *A61B 17/12* | (2006.01) |

(Continued)

(52) U.S. Cl.
CPC ...... *A61B 17/3468* (2013.01); *A61B 17/0057* (2013.01); *A61M 25/09* (2013.01); *A61B 17/12113* (2013.01); *A61B 17/3415* (2013.01); *A61B 17/3439* (2013.01); *A61B 2017/00243* (2013.01); *A61B 2017/00292* (2013.01); *A61B 2017/00575* (2013.01); *A61B 2017/00606* (2013.01); *A61B 2017/00623* (2013.01); *A61B 2017/12095* (2013.01); *A61F 2/011* (2020.05); *A61M 25/0054* (2013.01); *A61M 2025/09133* (2013.01); *A61M 2025/09183* (2013.01); *A61M 2025/09191* (2013.01)

(58) Field of Classification Search
CPC combination set(s) only.
See application file for complete search history.

(56) References Cited

U.S. PATENT DOCUMENTS

| | | | |
|---|---|---|---|
| 6,458,137 B1 * | 10/2002 | Klint | A61B 17/12022 606/108 |
| 9,180,004 B2 | 11/2015 | Alkhatib | |
| 2010/0168619 A1 | 7/2010 | Elsesser | |

(Continued)

FOREIGN PATENT DOCUMENTS

EP 0616544 B2 12/2000

OTHER PUBLICATIONS

International Search Report and Written Opinion in International Application No. PCT/US2018/019441 dated May 8, 2018.

*Primary Examiner* — Sameh R Boles
(74) *Attorney, Agent, or Firm* — Armstrong Teasdale LLP

(57) ABSTRACT

The present disclosure describes delivery cables for delivering a medical device. In one embodiment, a delivery cable includes a flexible inner core, a proximal outer coil, and a distal outer coil. The proximal outer coil has a first rigidity. The distal outer coil surrounds at least a portion of a distal section of the flexible inner core and has a second rigidity less than the first rigidity thereby, thereby reducing bias placed on the medical device by the delivery cable.

13 Claims, 12 Drawing Sheets

(51) Int. Cl.
*A61M 25/00* (2006.01)
*A61F 2/01* (2006.01)

(56) References Cited

U.S. PATENT DOCUMENTS

| | | |
|---|---|---|
| 2014/0052238 A1 | 2/2014 | Wang |
| 2014/0336572 A1 | 11/2014 | Heisel |
| 2015/0190230 A1 | 7/2015 | Tegg |
| 2017/0000495 A1* | 1/2017 | Le .................... A61B 17/12145 |

* cited by examiner

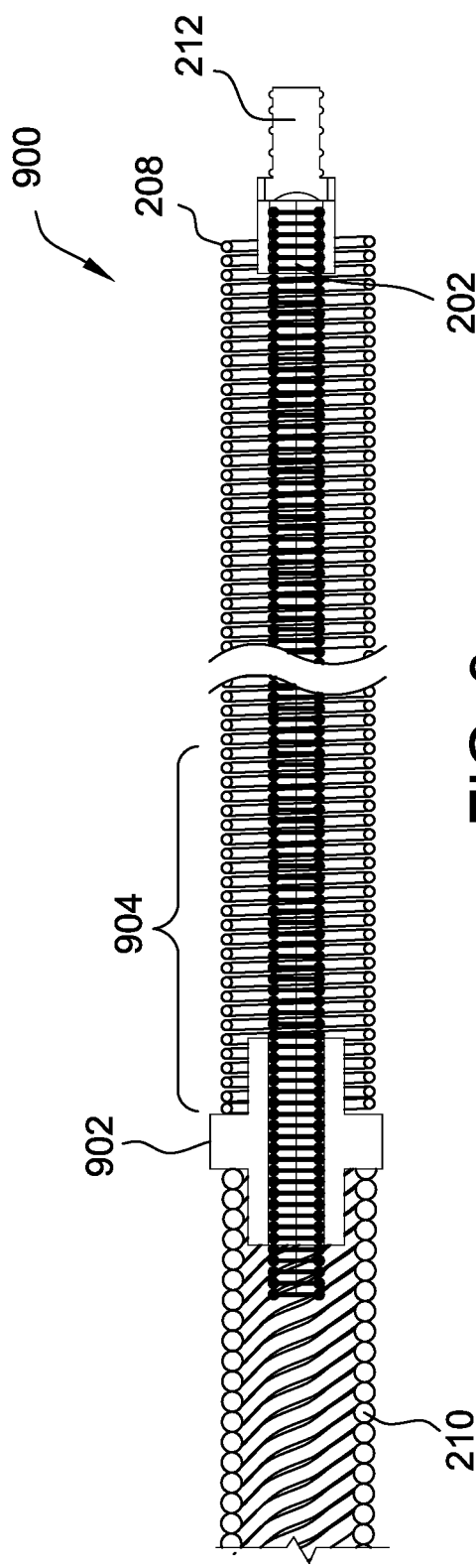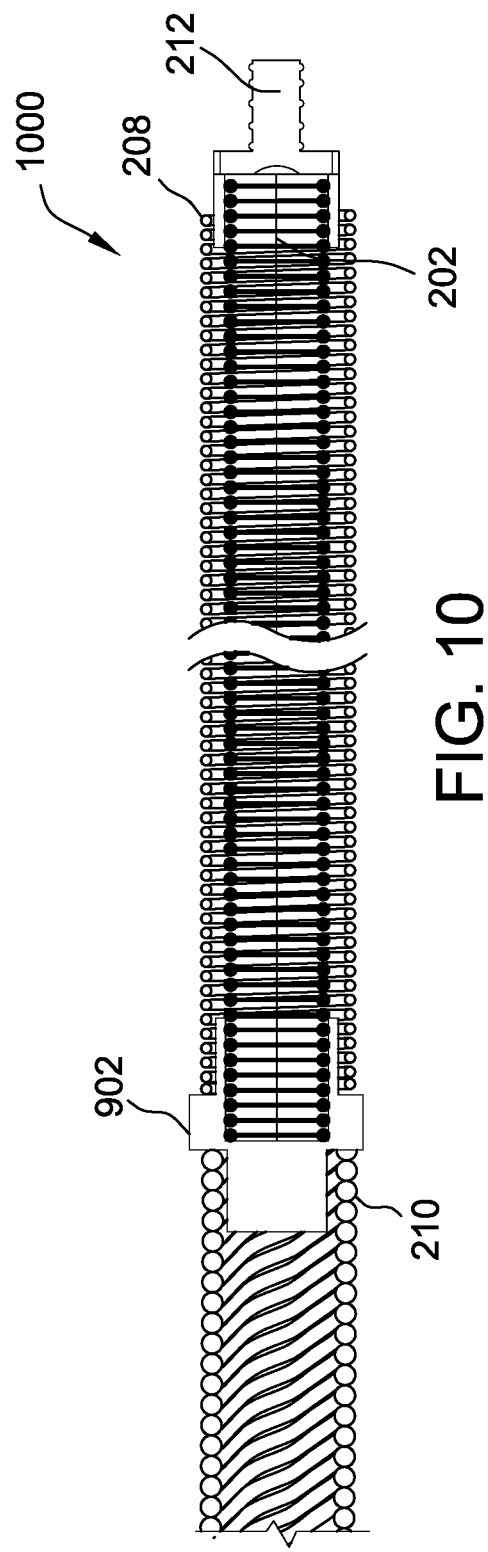

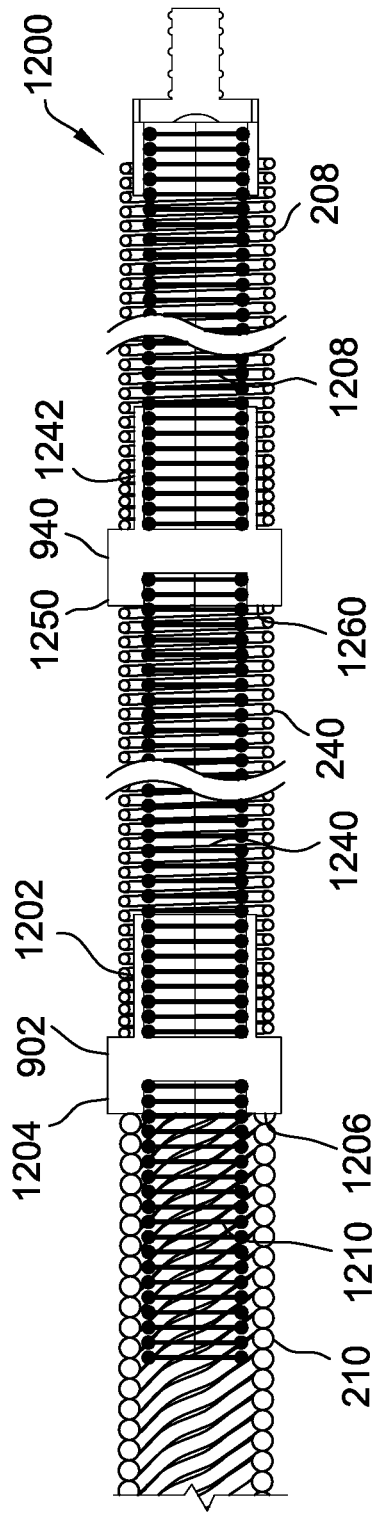
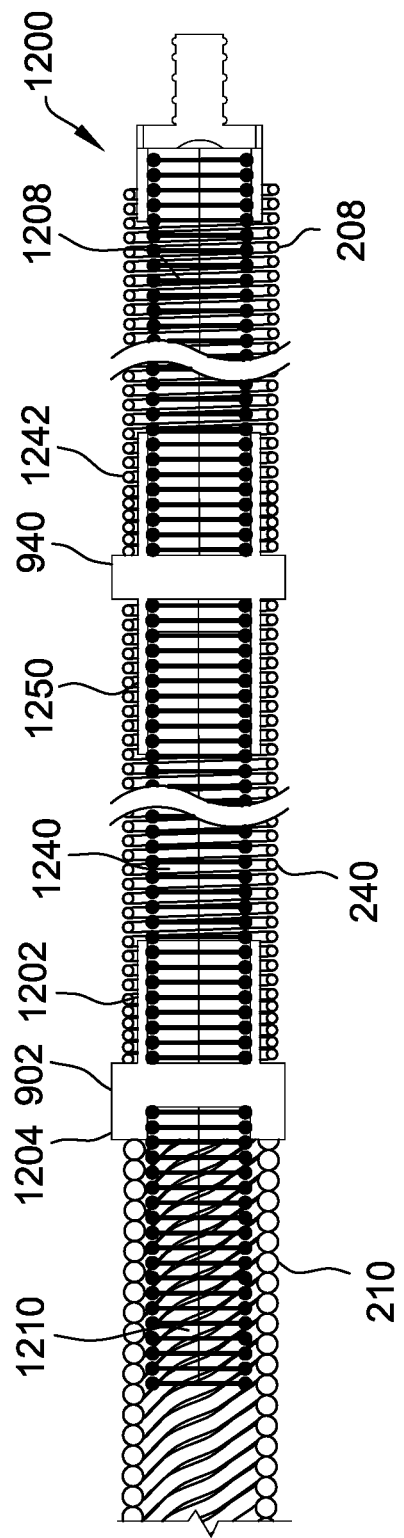
FIG. 12
FIG. 13

FLEXIBLE TORQUE CABLE FOR DELIVERY OF MEDICAL DEVICES

CROSS REFERENCE OF RELATED APPLICATIONS

This application claims priority to U.S. Provisional Application Ser. Nos. 62/462,661, filed Feb. 23, 2017; 62/478,883, filed Mar. 30, 2017; and 62/503,061, filed May 8, 2017 which are incorporated by reference in their entirety.

BACKGROUND OF THE DISCLOSURE a. Field of Disclosure

The present disclosure generally relates to a medical device delivery cable and methods of making and using the same. In particular, the present disclosure relates to a medical device delivery cable including a flexible inner member, a proximal outer member to provide column strength and rigidity to the delivery cable, and a distal outer member to provide flexibility to the delivery cable. Methods of manufacturing and using the medical device delivery cables are also disclosed.

b. Background Art

Delivery devices including, among other components, catheters and delivery cables are used for an ever-growing number of procedures, and in particular, for the delivery of medical devices to a target site. Typically, the catheter is manipulated through the patient's vasculature and to the intended site, for example, a site within the patient's heart or other organ and the delivery cable is used to advance the medical device through the catheter and to the target site. Once the medical device has reached the target site, the delivery cable may be detached or uncoupled from the medical device such that the medical device is deployed from both the catheter and the delivery cable.

Generally, the catheter would have an overall outside diameter small enough to negotiate blood vessels or other anatomy while retaining an inner diameter ("bore size") large enough to accommodate the medical device (and delivery cable) therethrough. Since the path within the patient may be long, tortuous, and/or involve intricate placement of a medical device(s), maneuverability via steering the catheter may be particularly beneficial. Furthermore, the delivery cable must be rigid enough so as to be capable of maneuvering the medical device through the catheter while still being flexible enough to accommodate the tortuous path through which it must travel to the target site.

SUMMARY OF THE DISCLOSURE

The present disclosure is directed to a delivery cable that includes a flexible inner core, a proximal outer coil having a first rigidity, and a distal outer coil surrounding at least a portion of a distal section of the flexible inner core and having a second rigidity less than the first rigidity, thereby reducing bias placed on the medical device by the delivery cable.

The present disclosure is further directed to a delivery device for delivering a medical device to a target site, the delivery device including an outer sheath, and a delivery cable positioned within the outer sheath and movable along a longitudinal axis with respect to the outer sheath. The delivery cable includes a flexible inner core, a proximal outer coil having a first rigidity, and a distal outer coil surrounding at least a portion of a distal section of the flexible inner core and having a second rigidity less than the first rigidity, thereby reducing bias placed on the medical device by the delivery cable.

The present disclosure is further directed to a method for implanting a medical device at a target site in a subject using a delivery cable and a delivery sheath. The method includes deploying the delivery sheath into the subject. The method further includes advancing the delivery cable through the deployed delivery sheath, the delivery cable including a flexible inner core, a proximal outer coil having a first rigidity, and a distal outer coil surrounding at least a portion of a distal section of the flexible inner core and having a second rigidity less than the first rigidity, wherein the relative dimensions of an outer diameter of the distal outer coil and an inner diameter of the delivery sheath reduce snaking of the delivery cable within the delivery sheath. The method further includes continuing to advance the delivery cable until the medical device exits the delivery sheath and reaches the target site, wherein the distal outer coil and flexible inner core reduce bias placed on the medical device by the delivery cable when the distal outer coil and flexible inner core are in a bent configuration. The method further includes deploying the medical device at the target site by detaching the medical device from the delivery cable.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 9 is a longitudinal cross-sectional view of one embodiment of a delivery cable including a coupler that may be used with the assembly shown in FIG. 1;

FIG. 10 is a longitudinal cross-sectional view of another embodiment of a delivery cable including a coupler that may be used with the assembly shown in FIG. 1;

FIG. 12 is a longitudinal cross-sectional view of another embodiment of a delivery cable including multiple couplers that may be used with the assembly shown in FIG. 1;

FIG. 13 is a longitudinal cross-sectional view of another embodiment of a delivery cable including multiple couplers that may be used with the assembly shown in FIG. 1;

DETAILED DESCRIPTION OF THE DISCLOSURE

Figure 1:
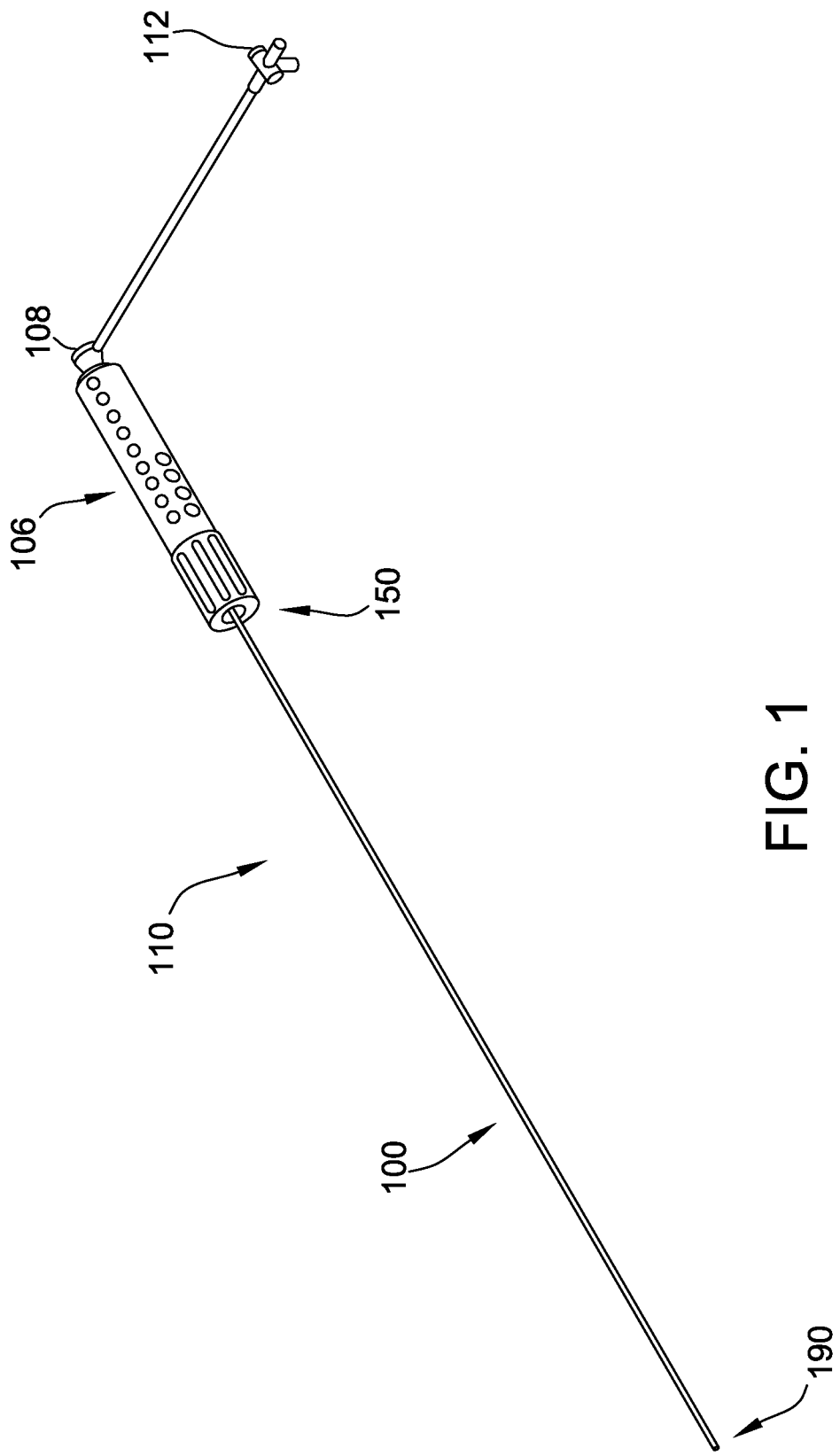
FIG. 1 is a perspective view of one embodiment of an introducer or catheter assembly in which the principles described herein may be implemented.

Septal occluders or other collapsible medical devices may be delivered through a catheter or delivery sheath and to a target site using a relatively stiff delivery cable. The stiffness of the delivery cable provides the column strength required to push the occluder through the catheter. However, the stiffness of the cable may also tend to pull and/or bias the occluder after deployment and prior to release of the occluder from the delivery cable, creating unpredictability in the occluder's final position. Further, although at least some delivery cables include a flexible distal section, the flexible distal section may cause the delivery cable to "snake," or curve, during advancement through the delivery sheath, which may result in an increase in the force required to advance the septal occluder.

Accordingly, the present disclosure is directed to a delivery cable comprising a rigid proximal portion and a flexible distal portion. The delivery cable is configured so as to have sufficient torque and column strength sufficient to deliver a medical device to a target site while also having sufficient flexibility to navigate through a patient's vasculature and to reduce movement of a medical device upon deployment of the medical device from the delivery cable.

The systems and methods described herein provide a delivery cable that includes a stiff proximal section to provide column strength and a flexible distal section to reduce an amount of bias that the delivery cable places on a medical device being delivered (e.g., a collapsible medical device, such as an occluder). The delivery cable includes a flexible inner member, or core, a more rigid proximal outer member, and a flexible distal outer member surrounding a distal portion of the flexible inner member. The rigid proximal outer member is configured to provide sufficient column strength to assist in delivering the medical device through a catheter or delivery sheath and sufficient torque to assist in removing the medical device from the delivery cable via rotation of the delivery cable, even in tortuous or challenging anatomy.

In contrast, the flexible distal outer member provides increased flexibility to the delivery cable during release of the medical device from the delivery cable upon deployment of the medical device. That is, the increased flexibility of the distal portion of the delivery cable reduces the tendency of the medical device to move, "jump," pull, or bias upon detaching the delivery cable from the medical device, which increases the predictability of the final position of the medical device after deployment thereof.

Further, the distal outer member of the delivery cables described herein have an outer diameter sized so as to reduce "snaking," curving, or bunching of the delivery cable during advancement through the catheter or other delivery sheath. In particular, by increasing the outer diameter of the delivery cable at the distal end thereof (as compared to outer diameter of the flexible inner member alone) such that it approximates the inner diameter of the catheter or delivery sheath through which it is advanced during delivery of a medical device, the ability of the delivery cable to "snake," curve, or bunch within the catheter or delivery sheath is reduced, thus reducing the amount of force necessary to advance the medical device through the catheter or delivery sheath. Further, by configuring the distal outer member to have a relatively short length as compared to the delivery cable overall, the ability of the delivery cable to "snake," curve, or bunch within the catheter or delivery sheath is further reduced.

Referring now to the Figures, FIG. 1 is a perspective view of a catheter assembly or introducer assembly 110 according to one embodiment including a catheter or an introducer 100 having a proximal portion 150 and a distal portion 190. Introducer 100 may be operably connected to a handle assembly 106 which assists in guiding or steering the introducer during procedures. Introducer assembly 110 further includes a hub 108 operably connected to an inner lumen (not shown) within the handle assembly 106 for insertion or delivery of catheter assemblies, fluids, or any other devices known to those of ordinary skill in the art. Optionally, introducer assembly 110 further includes a valve 112 operably connected to hub 108.

Figure 2:
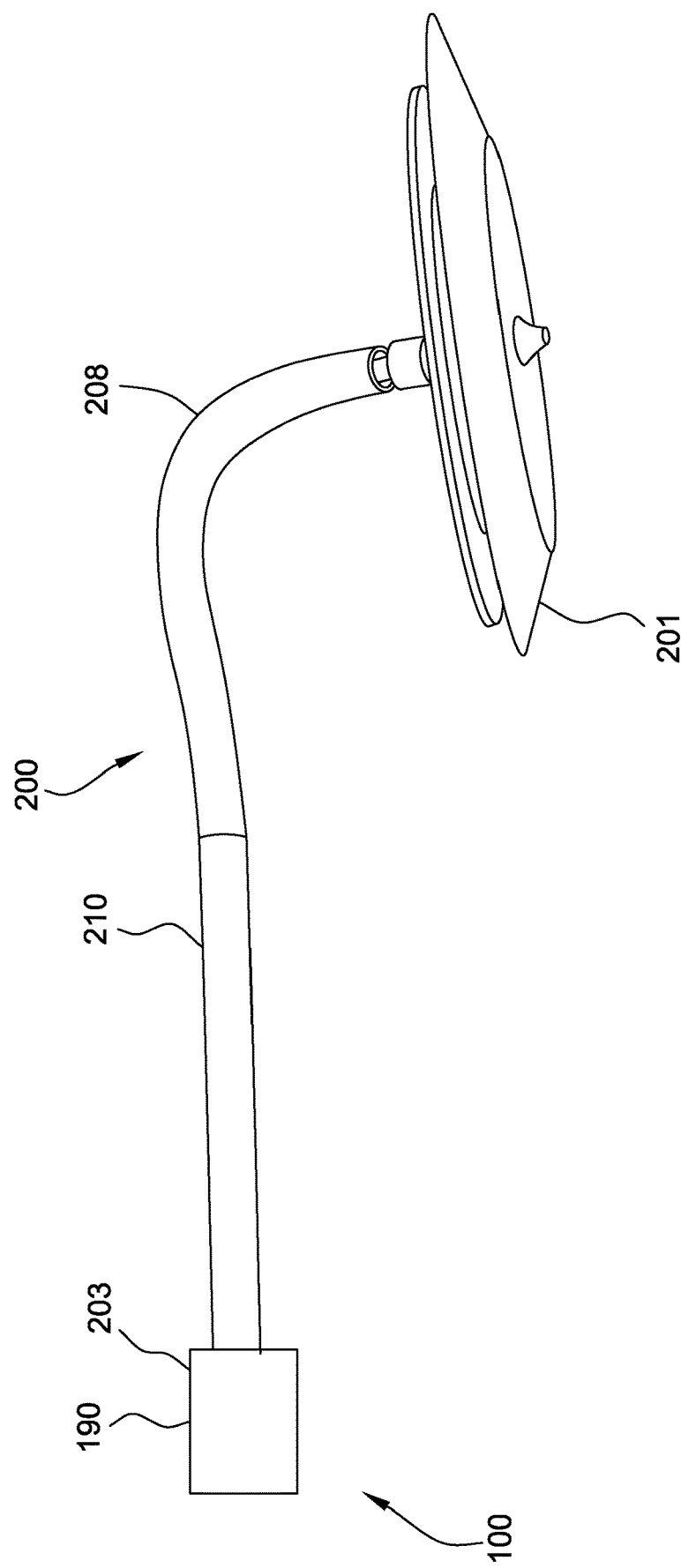
FIG. 2 is a schematic diagram of a portion of the assembly shown in FIG. 1 in combination with one embodiment of a delivery cable and a medical device.
Figure 3:
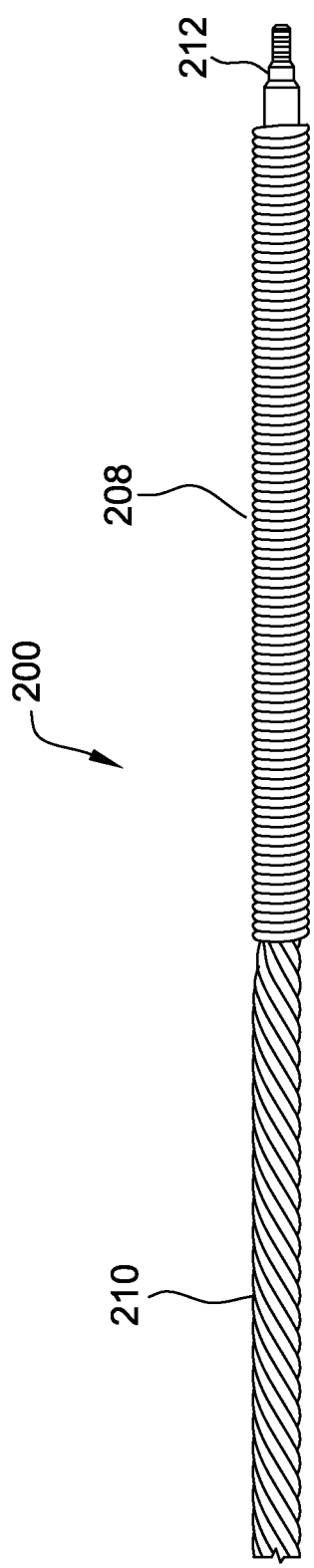
FIG. 3 is a perspective view of the delivery cable shown in FIG. 2.

FIG. 2 is a schematic diagram of a portion of introducer 100 shown in FIG. 1 in combination with one embodiment of a delivery cable 200 and a medical device 201. As shown in FIG. 2, delivery cable 200 extends from distal portion 190 of introducer 100 (i.e., a delivery sheath 203 of introducer 100), and is coupled to medical device 201. In this embodiment, medical device 201 is a collapsible occluder. Alternatively, medical device 201 may be any device capable of being coupled to delivery cable 200. FIG. 3 is a perspective view of the delivery cable 200. As described in detail below, delivery cable 200 includes a distal outer member 208, a proximal outer member 210, an inner member 202 (not shown in FIG. 3), and an endscrew 212.

Figure 4:
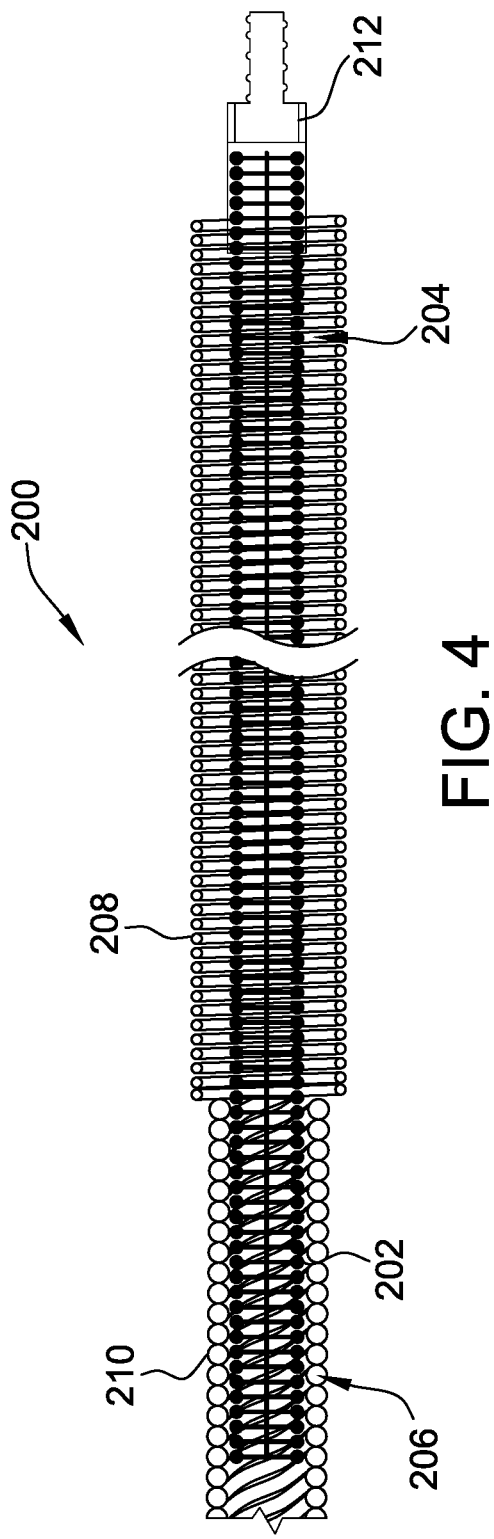
FIG. 4 is a longitudinal cross-sectional view of the delivery cable shown in FIG. 2.

FIG. 4 is a longitudinal cross-sectional view of delivery cable 200. Delivery cable 200 may be used to facilitate delivering a medical device such as, but not limited to, a collapsible occluder or the like. It should be noted that although delivery cable 200 is described herein as being useful in combination with introducer 100 illustrated in FIGS. 1 and 2, delivery cable 200 may be used in the delivery process of many various medical devices and in combination with many various sheaths, loaders, valves, etc.

As shown in FIG. 4, delivery cable 200 includes a flexible inner member (also referred to herein as a flexible core) 202. Delivery cable 200 has a distal section 204 and a proximal section 206. At least a portion of inner member 202 is surrounded by a distal outer member or coil 208 at distal section 204, and at least a portion of inner member 202 is surrounded by a proximal outer member or coil 210 at proximal section 206. An endscrew 212 is coupled to a distal end of inner member 202 to facilitate selectively attaching and detaching a medical device to delivery cable 200. For example, endscrew 212 may include a threaded portion configured to cooperate with a corresponding threaded portion positioned on or within the medical device to be delivered such that the medical device may be engaged or disengaged (i.e., coupled to or released from) delivery cable 200 upon rotation of delivery cable 200, and thus rotation of endscrew 212. Endscrew 212 is attached to inner member 202 via any method suitable to sufficiently secure endscrew 212 to inner member 202. For example, suitable methods include, but are not limited to, bonding via an adhesive (such as an epoxy), connecting (e.g., using a coupling member, such as a stainless steel tube or platinum-iridium marker band that is dome welded to a distal end of inner member 202 prior to being crimp or spot welded to endscrew 212), soldering, welding, spot welding or crimp welding, clamping, swaging, crimping, or any combination thereof. Endscrew 212 and inner member 202 may also be integrally formed (e.g., an overmolded screw). Further, in other embodiments, as an alternative to endscrew 212, any suitable device for attaching and detaching a medical device may be used.

Inner member 202 is formed of any material and has any configuration suitable to provide both torque strength and flexibility to delivery cable 200 and enables delivery cable 200 to function or operate as described herein. For example, inner member 202 may be configured so as to optimize torque strength and/or flexibility by modifying a length of inner member 202, a diameter or number of wires that may form inner member 202, a number of layers forming inner member 202, and/or the winding direction for each such layer.

Figure 6:
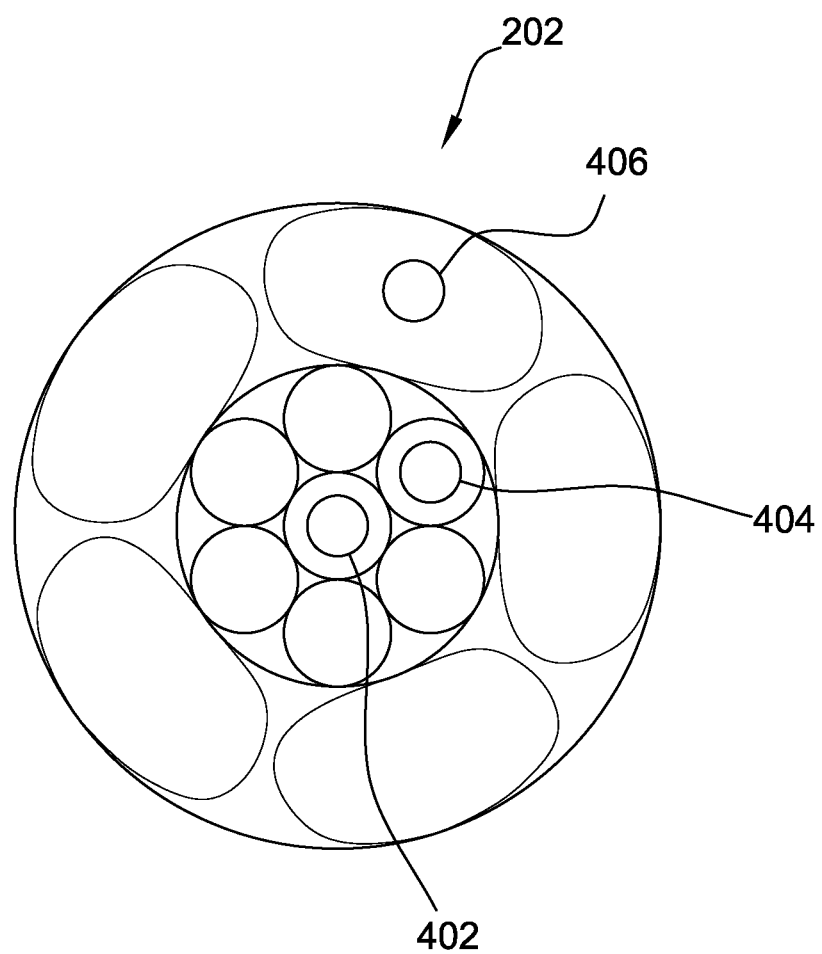
FIG. 6 is an axial cross-sectional view of a flexible inner member according to one embodiment that may be used with the delivery cable shown in FIG. 4 or FIG. 5.

For example, in one embodiment, inner member 202 is a multi-filar nitinol or stainless steel core that has a 1×7+5 construction. In this embodiment, as illustrated in FIG. 6 and discussed in more detail below, inner member 202 includes two outer layers formed using right-hand wound nitinol wires, and has an outer diameter of approximately 0.0303 inches (0.76962 millimeters (mm)). In other embodiments, inner member 202 may have an outer diameter from 0.02 inches (0.508 mm) to 0.060 inches (1.524 mm), including but not limited to about 0.02 inches (0.508 mm), about 0.03 inches (0.762 mm), about 0.04 inches (1.016 mm), about 0.05 inches (1.27 mm), and about 0.06 inches (1.524 mm).

The orientation of the outer two layers of nitinol wires of inner member 202 (i.e., both right-hand wound), aides in providing maximum torque strength during release or disengagement of a medical device from delivery cable 200 during deployment thereof (and an increased flexibility and torque strength as compared to as least some other known delivery cables). In an alternative embodiment, the outer two layers may be oriented in opposite directions (i.e., one right-hand wound and one left-hand wound) so as to create a bi-directional torque. Further, in some embodiments, inner member 202 may include a tapered configuration so as to provide a transition from a more rigid proximal portion to a more flexible distal portion. In such embodiments, the outer diameter of inner member 202 could range from 0.020 inches to 0.060 inches depending on the desired flexibility and torque strength.

As noted above, proximal outer member 210 surrounds inner member 202 at a proximal section 206 thereof. Inner member 202 extends through any length of proximal outer member 210 sufficient to enable the coupling or attaching of inner member 202 to proximal outer member 210. For example, as shown in FIG. 4, inner member 202 may only extend through a portion of the length of proximal outer member 210, wherein the section of overlap between inner member 202 and proximal outer member 210 (i.e., the length of delivery cable 200 along which inner member 202 extends through proximal outer member 210) is sufficient to enable the coupling thereof. In other embodiments, however, inner member 202 may extend through an entire length of proximal outer member 210. Still in other embodiments, inner member may include a proximal portion extending through proximal section 206 and a separate distal portion extending through distal section 204, as is further illustrated with respect to FIG. 11 and further described below. In this particular embodiment, the outer diameter and overall configuration of inner member 202 at proximal section 206 may be the same or different than the outer diameter and overall configuration of inner member 202 at distal section 204.

Proximal outer member 210 may be coupled or attached to inner member 202 by any suitable means. For example, in one embodiment, proximal outer member 210 is adhesively attached to inner member 202 via an epoxy placed along the entire overlapping surface of proximal outer member 210 or on only a portion thereof. In other embodiments, proximal outer member 210 is attached or coupled to inner member 202 by soldering, welding, spot or crimp welding, clamping, swaging, crimping, with any suitable adhesive, or any combination thereof.

Proximal outer member 210 is also coupled at a distal end thereof to a proximal end of distal outer member 208 by any suitable means. In one embodiment, proximal outer member 210 and distal outer member 208 are adhesively attached or coupled to one another via an epoxy. In other embodiments, proximal outer member 210 is attached or coupled to distal outer member 208 by welding, clamping, or with any suitable adhesive. Further, in some embodiments, a transition segment (not shown in FIG. 4) is positioned at an interface between distal outer member 208 and proximal outer member 210 to provide intermediate flexibility therebetween.

Proximal outer member 210 is sized and configured so as to provide sufficient column strength to delivery cable 200 to assist in delivering the medical device through a catheter or delivery sheath and sufficient torque to assist in releasing or disengaging the medical device from the delivery cable, even in tortuous or challenging anatomy. In one embodiment, proximal outer member 210 is a relatively stiff multi-filar cable formed of eight 0.0185 inch (0.4699 mm) stainless steel wires wound with an outer diameter of approximately 0.075 inches (1.905 mm) and an inner diameter of approximately 0.038 inches (0.9652 mm). In other embodiments, proximal outer member 210 may have an outer diameter from 0.05 inches (1.27 mm) to 0.085 inches (2.159 mm), including but not limited to about 0.05 inches (1.27 mm), about 0.06 inches (1.524 mm), about 0.07 inches (1.778 mm), about 0.08 inches (2.032 mm), and about 0.085 inches (2.159 mm). Proximal outer member 210 may be formed of any number of wires, having any size and shape, and arranged in any configuration suitable to provide the desired flexibility and strength of proximal outer member 210.

As illustrated in FIG. 4, distal outer member 208 surrounds inner member 202 and extends between proximal outer member 210 and endscrew 212. As described above, distal outer member 208 is attached or coupled to proximal outer member 210 by any suitable means. Distal outer member 208 is sized and configured so as to provide sufficient flexibility to delivery cable 200 to prevent the tendency of the medical device being delivered via delivery cable 200 to move, "jump," pull, or bias upon detaching the medical device from delivery cable 200 and to prevent undesired straightening of a delivery sheath during delivery of a medical device. Distal outer member 208 is further sized and configured so as to reduce the ability or tendency of delivery cable, and in particular a distal portion thereof, to "snake," curve, or bunch within the catheter or delivery sheath. In particular, distal outer member 208 has an outer diameter (e.g., 0.068 inches (1.727 mm) or 0.085 inches (2.159 mm)) that is slightly smaller than an inner diameter of a catheter or delivery sheath through which delivery cable 200 is advanced during delivery of a medical device. For example, distal outer member 208 may have an outer diameter that is greater than 50% of the inner diameter of the catheter or delivery sheath, including greater than 60%, greater than 70%, greater than 80%, and greater than 90% of the inner diameter of the catheter or delivery sheath, more particularly, an outer diameter that is greater than 95% of the inner diameter of the catheter or delivery sheath, and even more particularly, an outer diameter that is greater than 98% of the inner diameter of the delivery sheath. These percentages are exemplary. For example, those of skill in the art will appreciate that, for larger sheath diameters, different percentages may be more suitable. By keeping the space between the catheter or delivery sheath and the outer surface of distal outer member 208 minimized, the ability of distal outer member 208 to "snake," bunch, or curve within a catheter or delivery sheath during advancement of delivery cable 200 therethrough is reduced, which in turn, reduces the amount of force required to advance a medical device through the catheter or delivery sheath.

The ability or tendency of distal outer member 208 to "snake," curve, or bunch within a catheter or delivery sheath is further reduced by configuring distal outer member 208 to have a relatively short length as compared to the length of delivery cable 200 overall. For example, in one embodiment, distal outer member 208 has a length of approximately 1 inch (25.4 mm). In other embodiments, distal outer member 208 may have a length of from 0.5 inches (12.7 mm) to 9.5 inches (241.3 mm), including from 3 inches (76.2 mm) to 9.5 inches (241.3 mm), from 0.5 inches (12.7 mm) to 3.0 inches (76.2 mm), including but not limited to about 0.5 inches (12.7 mm), about 0.75 inches (19.05 mm), about 1.0 inches (25.4 mm), about 1.25 inches (31.75 mm), about 1.5 inches (38.1 mm), about 1.75 inches (44.45 mm), about 2.0 inches (50.8 mm), about 2.25 inches (57.15 mm), about 2.5 inches (63.5 mm), about 2.75 inches (69.85 mm), about 3.0 inches (76.2 mm), about 5 inches (127 mm), about 7 inches (177.8 mm), and about 9 inches (228.6 mm).

In one specific embodiment, distal outer member 208 has an outer diameter of approximately 0.085 inches (2.159 mm). In other embodiments, distal outer member 208 may have an outer diameter from 0.05 inches (1.27 mm) to 0.085 inches (2.159 mm), including but not limited to about 0.05 inches (1.27 mm), about 0.06 inches (1.524 mm), about 0.07 inches (1.778 mm), about 0.08 inches (2.032 mm), and about 0.085 inches (2.159 mm).

In one embodiment, distal outer member 208 includes tightly wound stainless steel wire having a diameter of from 0.011 inches (0.2794 mm) to 0.02 inches (0.3810 mm) forming a coil having an outer diameter of from 0.05 inches (1.27 mm) to 0.085 inches (2.159 mm) and a length of from 0.5 inches (12.7 mm) to 1.5 inch (38.1 mm). In one specific embodiment, distal outer member 208 includes tightly wound stainless steel wire having a diameter of approximately 0.014 inches (0.3566 mm) forming a coil having an outer diameter of approximately 0.068 inches (1.727 mm) and a length of approximately 1.0 inch (25.4 mm). In another specific embodiment, distal outer member 208 includes tightly wound stainless steel wire having a diameter of approximately 0.011 inches (0.2794 mm) forming a coil having an outer diameter of approximately 0.085 inches (2.159 mm) and a length of approximately 1.0 inch (25.4 mm). Accordingly, distal outer member 208, in one embodiment, may have a larger outer diameter than proximal outer member 210. In such an embodiment, a connector may optionally be positioned between a distal end of proximal outer member 210 and a proximal end of distal outer member 208 so as to provide a smooth transition between the differing outer diameters. In other embodiments, distal outer member 208 and proximal outer member 210 may have substantially equal outer diameters. As will be understood by those of skill in the art, the pitch, diameter, and/or material of distal outer member 208 may be modified without departing from the scope of the disclosure. For example, distal outer member 208 may be nitinol in some embodiments.

Figure 5:
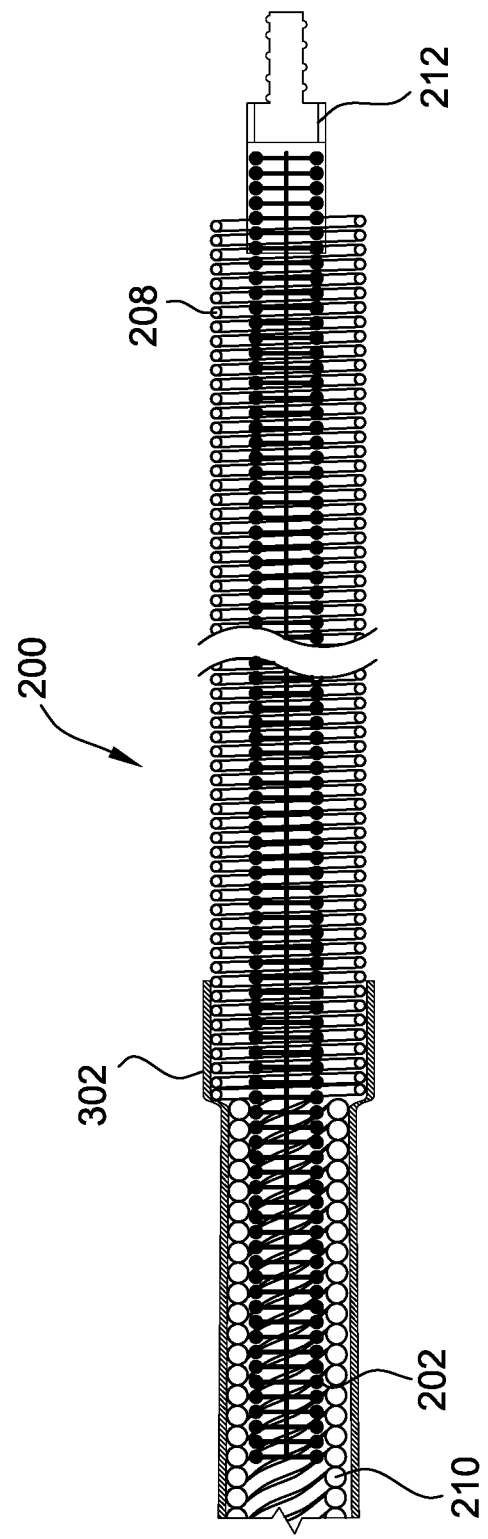
FIG. 5 is a longitudinal cross-sectional view of a delivery cable according to another embodiment that may be used with the assembly shown in FIG. 1.

FIG. 5 is a longitudinal cross-sectional view of delivery cable 200 illustrating a material that may be positioned over at least a portion of proximal outer member 210 to reduce the amount of air ingress during advancement of the medical device through a catheter or other delivery device. In one embodiment, at least a portion of the outer surface of proximal outer member 210, and in some embodiments an entire outer surface of proximal outer member 210, is coated, sealed, or surrounded by a heat shrink material suitable to reduce or prevent air ingress during advancement of the medical device during delivery thereof. The heat shrink material may also extend along a portion of distal outer member 208, which may increase the securement between proximal outer member 210 and distal outer member 208 and may also increase the lubriciousness of delivery cable 200 thus aiding in a smoother advancement of delivery cable 200 through a patient's vasculature. For example, as shown in FIG. 5, a heat shrink material 302 circumscribes at least a portion of both proximal outer member 210 and distal outer member 208. In other embodiments, heat shrink material 302 may circumscribe at least a portion of proximal outer member 210, including a proximal-most end thereof, but not circumscribe distal outer member 208. In yet another embodiment, heat shrink material 302 may circumscribe a distal end of proximal outer member 210 and a proximal end of distal outer member 208, but not circumscribe the proximal-most end of proximal outer member 210. Heat shrink material 302 may be formed of any heat shrink material suitable to reduce or prevent air ingress during advancement of the medical device during delivery thereof, to increase the securement between proximal outer member 210 and distal outer member 208, and/or to increase the lubricious of delivery cable 200 while not significantly increasing the outer diameter of delivery cable 200.

Delivery cable 200 may also include indicator marks or lines (not shown) on a proximal end thereof to convey the position of delivery cable 200 with respect to a delivery sheath or other delivery device to a user. In some embodiments, the indicator marks or lines are pad printed or laser etched on heat shrink material 302. In other embodiments, the indicator marks or lines are laser etched on a portion of proximal outer member 210. In still other embodiments, a colored heat shrink material including the indicator marks or lines, or indicating longitudinal placement by varying colors, may be placed on the outer surface of proximal outer member 210 prior to heat shrink material 302 being applied to delivery cable 200.

FIG. 6 is an axial cross-sectional view of flexible inner member 202. In this specific embodiment, inner member 202 includes a core layer 402, a first outer layer 404 surrounding core layer 402, and a second outer layer 406 surrounding first outer layer 404. In the specific embodiment, core layer 402 includes a single wire having a diameter of approximately 0.0055 inches (0.1397 mm), first outer layer 404 includes six wires each having a diameter of approximately 0.0051 inches (0.12954 mm), and second outer layer 406 includes five wires each having a diameter of approximately 0.0075 inches (0.1905 mm). In other embodiments, core layer 402 may include a single wire having a diameter from 0.0045 inches (0.1143 mm) inches to 0.010 inches (0.254 mm), including but not limited to about 0.0045 inches (0.1143 mm), about 0.0047 inches (0.11938 mm), about 0.0049 inches (0.12446 mm), about 0.0051 inches (0.12954 mm), about 0.0053 inches (0.13462 mm), about 0.0055 inches (0.1397 mm), about 0.006 inches (0.1524 mm), about 0.007 inches (0.1778 mm), about 0.008 inches (0.2032 mm), about 0.009 inches (0.2286 mm), and about 0.010 inches (0.254 mm). Further, first outer layer 404 may include any suitable number of wires each having a diameter from 0.0050 inches (0.127 mm) inches to 0.010 inches (0.254 mm), including but not limited to about 0.0050 inches (0.127 mm) inches, about 0.00525 inches (0.13335 mm), about 0.0055 inches (0.1397 mm), about 0.00575 inches (0.14605 mm), about 0.0060 inches (0.1524 mm), about 0.007 inches (0.1778 mm), about 0.008 inches (0.2032 mm), about 0.009 inches (0.2286 mm), and 0.010 inches (0.254 mm). In addition, second outer layer 406 may include any suitable number of wires each having a diameter from 0.0070 inches (0.1778 mm) to 0.015 inches (0.381 mm), including but not limited to about 0.0070 inches (0.1778 mm) inches, about 0.00725 inches (0.18415 mm), about 0.0075 inches (0.1905 mm), about 0.00775 inches (0.19605 mm), about 0.0080 inches (0.2032 mm), about 0.0090 inches (0.2286 mm), about 0.010 inches (0.254 mm), about 0.011 inches (0.2794 mm), about 0.012 inches (0.3048 mm), about 0.013 inches (0.3302 mm), about 0.014 inches (0.3556 mm), and about 0.015 inches (0.381 mm).

Alternatively, inner member 202 may include any configuration or size of wires that enables inner member 202 to function as described herein. That is, inner member 202 may include any configuration that facilitates achieving a balance between flexibility and torque strength as described herein. For example, in one embodiment, core layer 402 may be absent from inner member 202. In other embodiments, inner member 202 may include a 1×3, 1×7, 1×7+5, 1×12 or any other similar configuration. Using a wound construction with multiple layers for inner member 202 facilitates improving torque strength and flexibility. Further, each layer of inner member 202 may be formed from any suitable material known in the art. For example, in one specific embodiment, each wire of second outer layer 406 may be formed from stainless steel, or any other suitable, weldable material, while each wire of first outer layer 404 and core layer 402 may be formed of nitinol. Such a configuration provides an increased weld strength between inner member 202 and endscrew 212 and/or couplers 902 and 940, while maintaining a desired flexibility.

Figure 7:
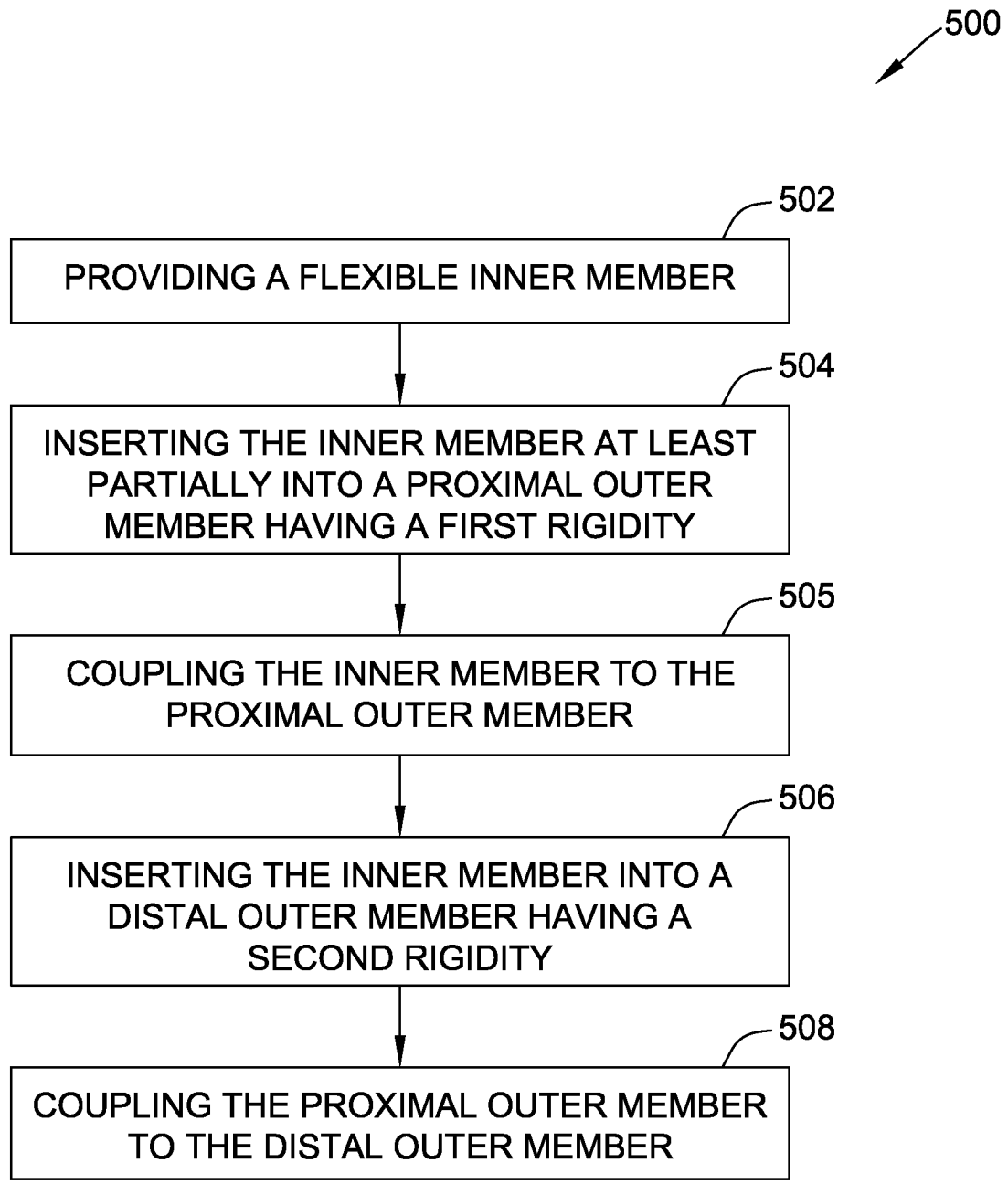
FIG. 7 is a flow diagram of a method of manufacturing a delivery cable according to one embodiment.

FIG. 7 is a flow diagram of a method 500 for manufacturing a delivery cable, such as delivery cable 200 (shown in FIG. 4), according to one embodiment. Notably, the steps in method 500 may be performed in any suitable order, and are not limited to being performed in the order shown in FIG. 7. Further, similar steps of method 500 may be used for producing additional embodiments of a delivery cable, such as those illustrated in FIGS. 9-14 and described in more detail below.

Method 500 includes providing 502 a flexible inner member, such as flexible core 202. Method 500 further includes inserting 504 the inner member at least partially into a proximal outer member having a first rigidity, such as proximal outer member 210 and coupling 505 the inner member to the proximal outer member. Method 500 further includes inserting 506 the inner member into a distal outer member having a second rigidity, such as distal outer member 208. In this embodiment the inner member extends through an entire length of the distal outer coil so that the inner member can attach to the proximal outer member and an endscrew. Method 500 further includes coupling 508 the proximal outer member to the distal outer member. This coupling facilitates providing a smooth transition between the proximal outer member and the distal outer member, and may be accomplished, for example, using welding, a heat shrink material, or a coupler, as described herein.

Figure 8:
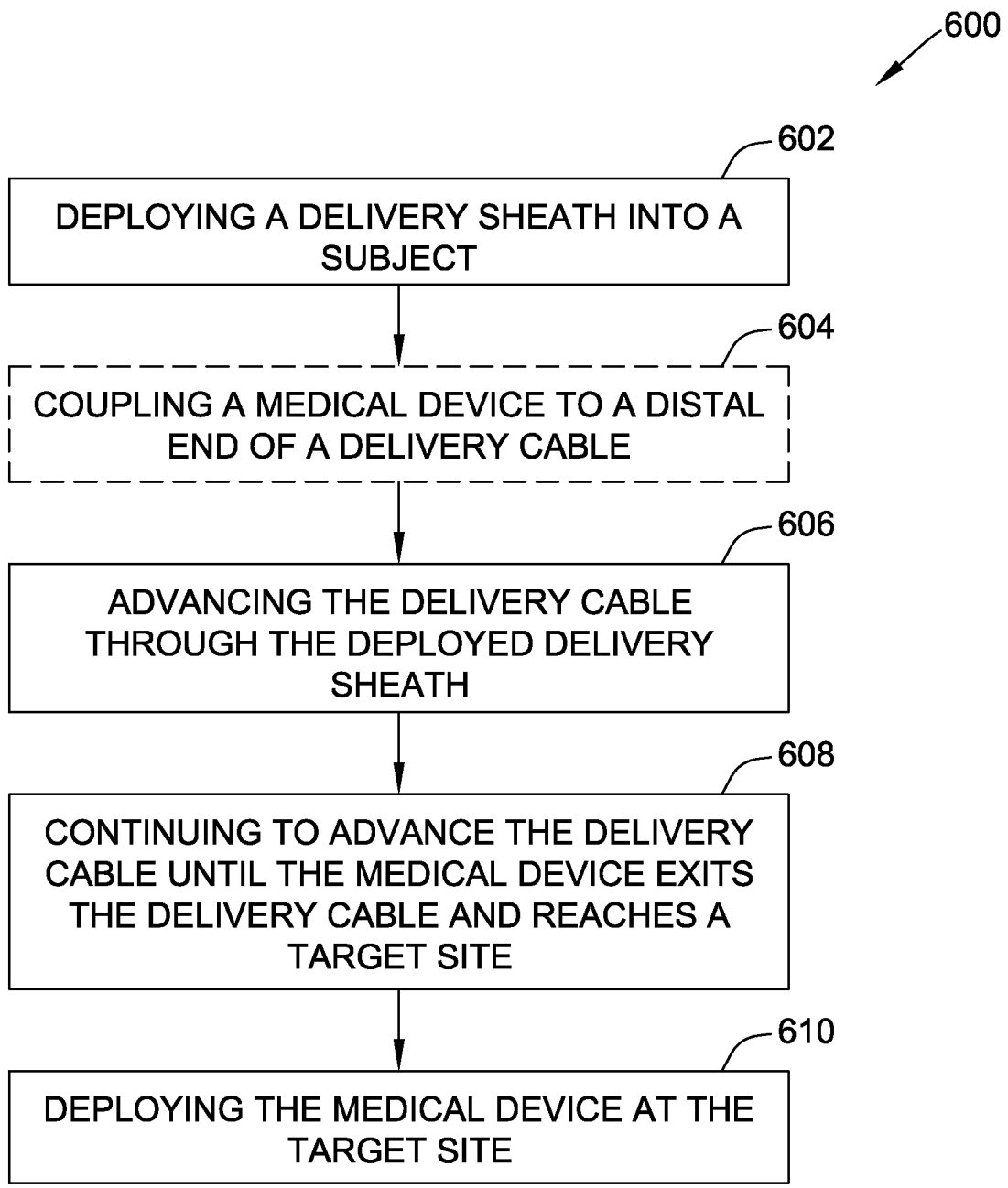
FIG. 8 is a flow diagram of a method for implanting a medical device at a target site according to one embodiment.

FIG. 8 is a flow diagram of a method 600 for implanting a medical device (e.g., collapsible occluder) at a target site in a subject using a delivery cable and a delivery sheath, such as delivery cable 200 and delivery sheath 203 (shown in FIG. 2), according to one embodiment. Notably, the steps in method 600 may be performed in any suitable order, and are not limited to being performed in the order shown in FIG. 8. Method 600 includes deploying 602 the delivery sheath into the subject. In some embodiments, the medical device is already attached to a distal end of the delivery cable in a "preloaded" configuration. Alternatively, in other embodiments, method 600 may optionally include coupling 604 the medical device to a distal end of the delivery cable. In the embodiments described herein, delivery cable has a sufficient column strength and tensile strength for delivering and recapturing the medical device. As described above, the delivery cable includes at least a flexible inner core, a proximal outer coil having a first rigidity, and a distal outer coil surrounding at least a portion of a distal section of the flexible inner core and having a second rigidity less than the first rigidity. Method 600 further includes advancing 606 the delivery cable through the deployed delivery sheath. As described above, the relative dimensions of an outer diameter of the distal outer coil and an inner diameter of the delivery sheath facilitate reducing snaking of the delivery cable within the delivery sheath. Method 600 further includes continuing 608 to advance the delivery cable until the medical device exits the delivery sheath and reaches the target site. At the target site, the relative rigidity of distal section of the delivery cable with respect to the proximal outer coil facilitates reducing bias placed on the medical device by the delivery cable when the distal outer coil is in a bent configuration, thus reducing moving, "jumping," pulling, or biasing upon detaching the delivery cable from the medical device. Method further includes deploying 610 the medical device at the target site by detaching the medical device from the delivery cable.

FIG. 9 is a longitudinal cross-sectional view of one embodiment of a delivery cable 900 including a coupler 902 that may be used with the assembly shown in FIG. 1. Delivery cable 900 includes inner member 202, distal outer member 208, proximal outer member 210, and endscrew 212. In this embodiment, as shown in FIG. 9, coupler 902 couples distal outer member 208 to proximal outer member 210. For example, coupler 902 may be attached to distal outer member 208 and proximal outer member 210 using a seam weld, spot weld, tack weld or crimp weld, and coupler 902 may be attached to inner member 202 using adhesive, soldering, a spot weld or crimp weld, clamping, crimping, or any combination thereof. Further, coupler 902 may be, for example, stainless steel. Alternatively, coupler 902 may be attached to distal outer member 208, proximal outer member 210, and/or inner member 202 using any suitable techniques (e.g., by using an additional coupling member such as a stainless steel tube or platinum-iridium marker band that is dome welded to a distal end of inner member 202 prior to being crimp or spot welded to coupler 902). Coupler 902 may be made of any material that enables delivery cable 900 to function as described herein, and facilitates a robust connection between distal outer member 208, proximal outer member 210, and inner member 202.

In the embodiment shown in FIG. 9, inner member 202 extends through the entirety of coupler 902, and into a portion of proximal outer member 210. In contrast, FIG. 10 is a longitudinal cross-sectional view of another embodiment of a delivery cable 1000. In this embodiment, inner member 202 extends through only a portion of coupler 902, and does not extend into proximal outer member 210. For example, in the embodiment of FIG. 10, inner member 202 may have an outer diameter (e.g., on the order of approximately 30 to 60 thousandths of an inch (0.762 to 1.524 mm)) that is too large to be received within proximal outer member 210.

Figure 11:
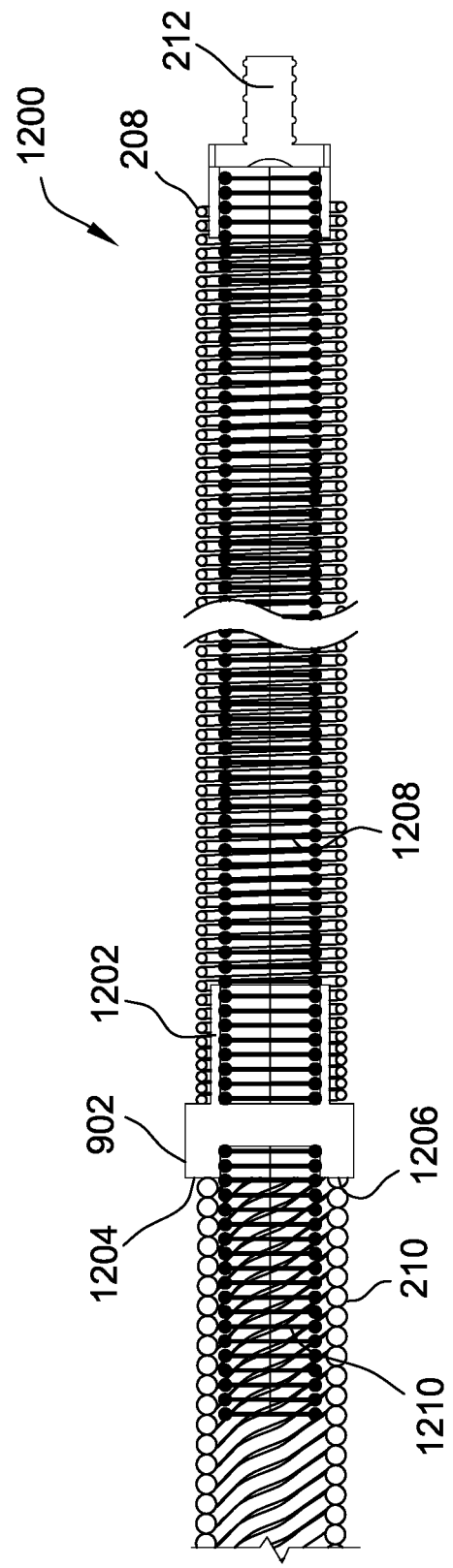
FIG. 11 is a longitudinal cross-sectional view of another embodiment of a delivery cable including a coupler that may be used with the assembly shown in FIG. 1.
Figure 14:
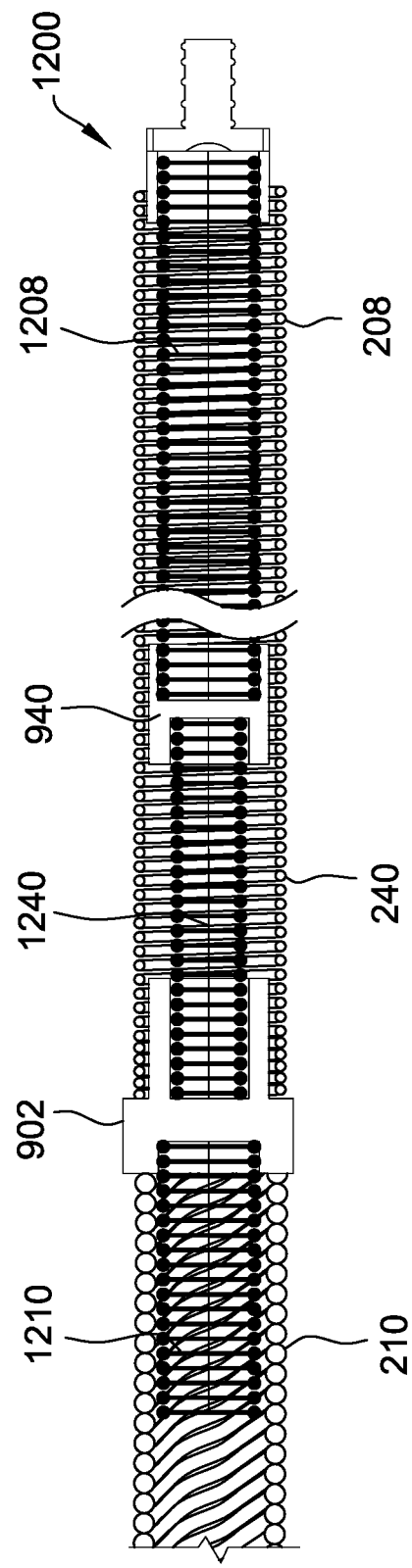
FIG. 14 is a longitudinal cross-sectional view of another embodiment of a delivery cable including multiple couplers that may be used with the assembly shown in FIG. 1.

Similarly, FIG. 11 is a longitudinal cross-sectional view of another embodiment of a delivery cable 1200 in which an inner member does not extend through the entirety of coupler 902. This particular embodiment includes a distal inner member 1208 and a separate proximal inner member 1210. Distal inner member 1208 extends into and is secured to a distal portion 1202 of coupler 902, and proximal inner member 1210 extends into and is secured to a proximal portion 1204 of coupler 902. A proximal end of distal outer member 208 wraps around and is secured to an outer circumference of coupler 902 at distal portion 1202, and a distal end of proximal outer member 210 wraps around proximal inner member 1210 and is secured to the proximal end surface 1206 of coupler 902. Distal inner member 1208, proximal inner member 1210, distal outer member 208, and proximal outer member 210 are attached or secured to coupler 902 in any suitable manner including using a seam weld, adhesive, a spot weld or crimp weld, clamping, crimping, or any combination thereof.

In some embodiments, the delivery cable may further include an intermediate portion positioned between a distal end of the proximal outer member and a proximal end of the distal outer member. Such an intermediate portion may be more flexible than a proximal-most portion of the delivery cable, but less flexible than a distal-most portion of the delivery cable. Such an intermediate portion may assist in reducing the amount of force applied to a delivery sheath or other delivery device during delivery of a medical device, thus reducing the tendency of the delivery sheath to straighten during delivery of a medical device while still maintaining sufficient column strength to deliver the medical device through the delivery sheath.

For example, FIG. 12 is a longitudinal cross-sectional view of an embodiment of a delivery cable 1200 including proximal outer member 210, distal outer member 208, and intermediate outer member 240. Proximal outer member 210 is coupled to intermediate outer member 240 by coupler 902, and intermediate outer member 240 is coupled to distal outer member 208 via coupler 940 in the same manner described above and illustrated in FIG. 11 with respect to coupler 902. As shown in FIG. 12, the inner member is formed of three separate and distinct portions, including distal inner member 1208, proximal inner member 1210, and intermediate inner member 1240, coupled or secured to one another via couplers 902 and 940. In particular, distal inner member 1208 extends into and is secured to a distal portion 1242 of coupler 940, and proximal inner member 1210 extends into and is secured to a proximal portion 1204 of coupler 902. A proximal end of intermediate inner member 1240 extends into and is secured to a distal portion 1202 of coupler 902, and a distal end of intermediate portion 1240 extends into and is secured to a proximal portion 1250 of coupler 940.

In one embodiment, illustrated in FIG. 12, each of coupler 902 and coupler 940 are configured similarly to coupler 902 illustrated in FIG. 11. In such an embodiment, a proximal end of distal outer member 208 wraps around and is secured to an outer circumference of coupler 940 at distal portion 1242, and a proximal end of intermediate outer member 240 wraps around and is secured to an outer circumference of coupler 902 at a distal portion 1202. A distal end of proximal outer member 210 wraps around proximal inner member 1210 and is secured to the proximal end surface 1206 of coupler 902, and a distal end of intermediate outer member 240 wraps around intermediate inner member 1240 and is secured to the proximal end surface 1260 of coupler 940.

In another embodiment illustrated in FIG. 13, coupler 940 is configured such that a distal end of intermediate outer member 240 wraps around and is secured to an outer circumference of proximal portion 1250 of coupler 940. In yet another embodiment illustrated in FIG. 14, coupler 940 couples only intermediate inner member 1240 and distal inner member 1208, while distal outer member 208 extends along the length of distal inner member 1208, coupler 940, and intermediate inner member 1240. In such an embodiment, coupler 940 may have a different inner diameter on a proximal end thereof and a distal end thereof to allow for the use of an intermediate inner member 1240 and a distal inner member 1208 of different outer diameters. Distal outer member 208 extends across the entire outer surface of coupler 940 in this embodiment.

In each of the embodiments described above, distal inner member 1208, proximal inner member 1210, and intermediate inner member 1240 as well as distal outer member 208, proximal outer member 210, and intermediate outer member 240 may be attached or secured to coupler 902 and coupler 940 in any suitable manner including using a seam weld, adhesive, soldering, a spot weld or crimp weld, clamping, crimping, swaging, or any combination thereof. Further, each of distal inner member 1208, proximal inner member 1210, and intermediate inner member 1240 as well as distal outer member 208, proximal outer member 210, and intermediate outer member 240 may have the same or different diameters from one another allowing for each component to be individually sized and configured to allow for the specifically desired strength and flexibility thereof, and couplers 902 and 940 may be oriented and positioned in any suitable configuration with respect to each of distal inner member 1208, proximal inner member 1210, and intermediate inner member 1240 as well as distal outer member 208, proximal outer member 210, and intermediate outer member 240 so as to form delivery cable 1200. In some embodiments, instead of having a substantially constant rigidity along its entire length, distal outer member 208 and/or inner member 202 at distal section 204 has a transition section 904 (shown in FIG. 9). In transition section 904, the rigidity of distal outer member 208 and/or inner member 202 decreases (i.e., increasing flexibility) as distal outer member 208 and/or inner member 202 extend away from proximal outer member 210. Transition section 904 may be sized such that distal outer member 208 includes a flexible portion (e.g., having a length of approximately 0.5 to 1.5 inches (12.7 to 38.1 mm)) extending beyond transition section 904, and such that the total length of transition section 904 and distal outer member 208 has a length of approximately 0.5 inches (12.7 mm) to 9.5 inches (241.3 mm), including 3 inches (76.2 mm) to 9.5 inches (241.3 mm), and including 5 inches (127 mm). For example, if distal outer member 208 has an overall length of approximately 3.0 inches (76.2 mm), transition section may have a length of approximately 2.0 inches to 2.5 inches (50.8 to 63.5 mm). Alternatively, transition section 904 may extend substantially the entire length of distal outer member

208. Transition section 904 (and/or the flexible portion) may have any dimensions that enable delivery cables 900 to function as described herein.

Transition section 904 may be formed or created in several different ways. In one example, distal outer member 208 may be a multi-strand cable, wherein transition section 904 is formed by tapering a wall thickness of distal outer member 208 using a swaging or grinding process. In another example, distal outer member 208 may be a nitinol cable (e.g., multi-strand or single wire, single layer or double layer), wherein transition section 904 is formed via a heat treatment that is varied along distal outer member 208. The varied heat treatment creates a gradual change in an Austenite finish temperature (Af) along distal outer member 208. In another example, transition section 904 is formed by varying a pitch of distal outer member 208. In yet another example, transition section 904 is formed by applying a variable thickness coating (e.g., a metallic and/or polymer coating) to distal outer member 208. In other embodiments (not shown), transition section 904 is formed at a portion of proximal outer member 210 as opposed to at a portion of distal outer member 208 and/or inner member 202. Such a transition section 904 may be formed in any of the methods described above, and may further include the tapering of a distal portion of a proximal inner member 1210, such as a proximal inner member illustrated in FIGS. 11-14.

In a further example, distal outer member 208 including transition section 904 is formed by welding two or more outer member segments together end-to-end, with the more distal outer member segments being more flexible than the more proximal outer member segments. The outer member segments may be multi-strand or single wire, single layer or multiple layers, round wire or flat wire, etc. Further, each outer member segment forming distal outer member 208 may have different construction and/or different wire diameters than the other outer member segments. In addition, the stiffness of each outer member segment may be varied using the techniques described above.

Figure 15:
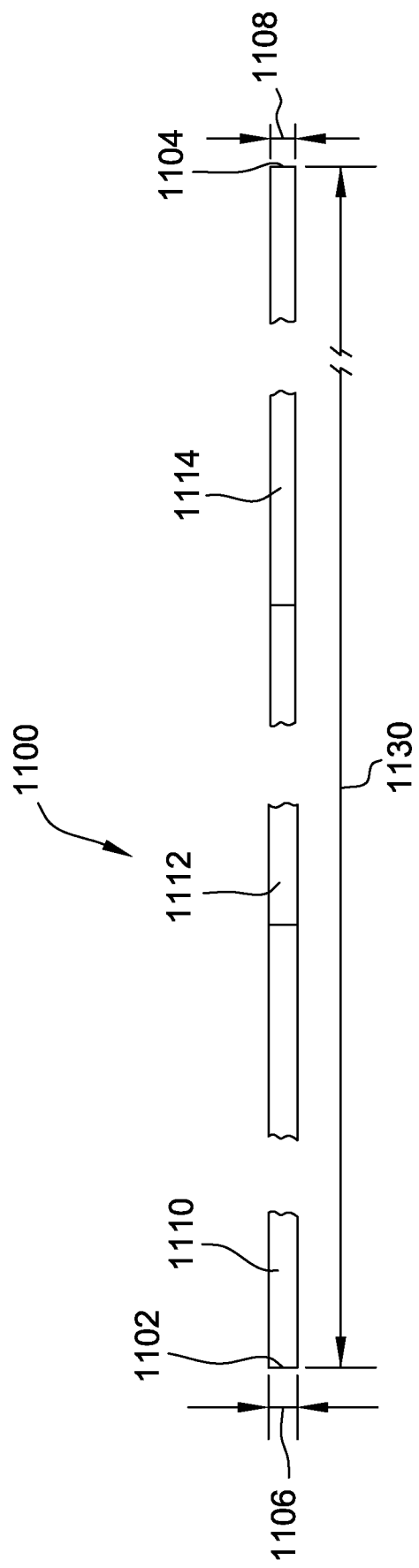
FIG. 15 is a schematic view of a tapered wire that may be used to form another embodiment of a distal outer member that may be used with the assembly shown in FIG. 1.

FIG. 15 is a schematic view of a tapered wire 1100 that may be used to form another embodiment of a distal outer member that may be used, for example, with the assembly shown in FIG. 1. Tapered wire 1100 may be formed, for example, using centerless grinding or other suitable techniques. Tapered wire 1100 extends from a proximal end 1102 to a distal end 1104. Further, tapered wire 1100 has a first diameter 1106 at proximal end 1102 and a second diameter 1108 at distal end 1104. In this embodiment, first diameter 1106 is larger than second diameter 1108. For example, first diameter 1106 may be in a range from approximately 0.013 inches to 0.025 inches (0.3302 to 0.635 mm), and second diameter 1108 may be in a range from approximately 0.006 to 0.017 inches (0.1524 to 0.4318 mm). Alternatively, first and second diameters 1106 and 1108 may have any dimensions that enable tapered wire 1100 to function as described herein.

In one embodiment, tapered wire 1100 includes a first segment 1110, a second segment 1112, and a third segment 1114. In this embodiment, first segment 1110 has a constant diameter (e.g., first diameter 1106), a diameter of second segment 1112 gradually tapers (e.g., from first diameter 1106 to second diameter 1108), and third segment 1114 has a constant diameter (e.g., second diameter 1108). Alternatively, tapered wire 1100 may include any number of segments having any dimensions that enable tapered wire 1100 to function as described herein.

To form the distal outer member, tapered wire 1100 is wound into a coil. The resulting distal outer member may have, for example, an overall length in a range from approximately 0.5 inches to 3.0 inches (12.7 to 76.2 mm), and more particularly, of approximately 1.5 inches (38.1 mm). Further, the resulting distal outer member may include a transition section (over which the rigidity of the transition distal outer member varies) having a length in a range from approximately 0.2 inches to 3.0 inches (5.08 to 76.2 mm), and more particularly, of approximately 0.5 inches (12.7 mm). Accordingly, tapered wire 1100 may have, for example, an overall length 1130 of approximately 30.0 inches (762 mm), and the distal outer member, including a transition section, may have an overall length of approximately 0.5 inches (12.7 mm) to 9.5 inches (241.3 mm), including 3 inches (76.2 mm) to 9.5 inches (241.3 mm), and including 5 inches (127 mm). Alternatively, tapered wire 1100 may have any overall length 1130, and the resulting distal outer member may have any total length and transition section length that enables tapered wire 1100 and the distal outer member to function as described herein.

As indicated above, tapered wire 1100 (or multiple tapered wires 1100) is wound into a coil to form the distal outer member. The coil may be tight wound, open wound, or transition between tight wound to open wound along its length. Transitioning from tight wound to open wound may be accomplished by using a consistent pitch (because the diameter of tapered wire 1100 changes along the length of tapered wire 1100). Alternatively, transitioning from tight wound to open wound may be accomplished using gradual changes in pitch along one portion or the entire length of the coil. Further, tapered wire 1100 may be used to form any outer member or inner member of the delivery cable described herein.

In other embodiments, instead of the distal outer member having a varying stiffness, and similar to the embodiment described above with respect to FIG. 14, the inner core has a varying stiffness. For example, in one such embodiment, the inner core is a solid tapered nitinol core wire, and the distal outer member is a flexible torque member (e.g., a flexible torque member formed from a multi-strand and/or a multi-layer coil or a flexible torque member that may be formed using a laser cut hypotube). In this embodiment, the nitinol core provides tensile strength for the delivery cable, and transitions from stiff to flexible, and the distal outer member (which may be formed of stainless steel or nitinol) provides at least a portion of the torque strength for the delivery cable. Further, in this embodiment, the inner core and distal outer member both terminate at both distal and proximal ends.

Although a number embodiments of this disclosure have been described above with a certain degree of particularity, those skilled in the art could make numerous alterations to the disclosed embodiments without departing from the spirit or scope of the disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A delivery cable for delivering a medical device, the delivery cable comprising:
    a flexible cylindrical inner core;
    a proximal outer coil having a first rigidity; and
    a distal outer coil surrounding at least a portion of a cylindrical distal section of the flexible cylindrical inner core and having a second rigidity less than the first rigidity, thereby reducing bias placed on the medical device by the delivery cable,
    wherein the distal outer coil comprises at least one first wound wire having a first wire diameter, and wherein the proximal outer coil comprises at least one second wound wire having a second wire diameter greater than the first wire diameter.

2. The delivery cable of claim 1, wherein the distal outer coil and the flexible cylindrical inner coil reduce snaking of the delivery cable when the delivery cable is advanced through an outer sheath.

3. The delivery cable of claim 1, wherein an outer diameter of the distal outer coil is approximately equal to an outer diameter of the proximal outer coil.

4. The delivery cable of claim 1, wherein an outer diameter of the distal outer coil is greater than an outer diameter of the proximal outer coil.

5. The delivery cable of claim 1, wherein the delivery cable further comprises:
    an endscrew coupled to a distal end of the flexible cylindrical inner core and configured to engage the medical device.

6. The delivery cable of claim 5, wherein the endscrew includes a threaded portion for engaging the medical device.

7. The delivery cable of claim 1, further comprising:
    a heat shrink material circumscribing at least a portion of both the proximal outer coil and the distal outer coil.

8. The delivery cable of claim 1, further comprising:
    a first coupler configured to couple the proximal outer coil to the distal outer coil.

9. The delivery cable of claim 8, further comprising:
    an intermediate outer coil, wherein the proximal outer coil and the intermediate outer coil are coupled to one another via the first coupler and wherein the intermediate outer coil and the distal outer coil are coupled to one another via a second coupler.

10. The delivery cable of claim 8, wherein the flexible cylindrical inner core comprises a proximal flexible cylindrical inner core, an intermediate flexible cylindrical inner core, and a distal flexible cylindrical inner core.

11. The delivery cable of claim 10, wherein the proximal flexible cylindrical inner core and the intermediate flexible cylindrical inner core are coupled to one another via the first coupler, and wherein the intermediate flexible cylindrical inner core and the distal flexible cylindrical inner core are coupled to one another via a second coupler.

12. The delivery cable of claim 1, wherein the distal outer coil includes a transition section, and wherein the distal outer coil has a varying rigidity along the transition section.

13. The delivery cable of claim 1, wherein the distal outer coil is a tapered wire wound into a coil.

* * * * *